United States Patent
Probasco

(10) Patent No.: US 8,414,934 B2
(45) Date of Patent: Apr. 9, 2013

(54) COMPOSITIONS AND METHODS FOR ARACHNID CONTROL

(75) Inventor: Gene Probasco, Yakima, WA (US)

(73) Assignee: John I. Haas, Inc., Washington, DC (US)

( * ) Notice: Subject to any disclaimer, the term of this patent is extended or adjusted under 35 U.S.C. 154(b) by 0 days.

(21) Appl. No.: 12/866,874

(22) PCT Filed: Feb. 6, 2009

(86) PCT No.: PCT/US2009/000767
§ 371 (c)(1),
(2), (4) Date: Mar. 15, 2011

(87) PCT Pub. No.: WO2009/099646
PCT Pub. Date: Aug. 13, 2009

(65) Prior Publication Data
US 2011/0159119 A1 Jun. 30, 2011

Related U.S. Application Data

(60) Provisional application No. 61/065,104, filed on Feb. 8, 2008.

(51) Int. Cl.
*A01N 65/00* (2009.01)

(52) U.S. Cl. .......................................................... 424/725

(58) Field of Classification Search .................... None
See application file for complete search history.

(56) References Cited

U.S. PATENT DOCUMENTS

| | | | |
|---|---|---|---|
| 3,615,660 A | 10/1971 | Bavisotto et al. |
| 3,886,171 A | 5/1975 | Parsons |
| 4,002,683 A | 1/1977 | Todd, Jr. |
| 4,148,873 A | 4/1979 | Owades |
| 4,170,638 A | 10/1979 | Owades |
| 4,281,061 A | 7/1981 | Zuk et al. |
| 4,562,794 A | 1/1986 | Speckman |
| 4,844,939 A | 7/1989 | Todd, Jr. |
| 4,847,292 A | 7/1989 | Katz et al. |
| 4,867,731 A | 9/1989 | Willard et al. |
| 5,082,975 A | 1/1992 | Todd, Jr. et al. |
| 5,158,788 A | 10/1992 | Lavens et al. |
| 5,166,449 A | 11/1992 | Todd, Jr. et al. |
| 5,227,162 A | 7/1993 | Ferrari |
| 5,286,506 A | 2/1994 | Millis et al. |
| 5,370,863 A | 12/1994 | Barney et al. |
| 5,372,817 A | 12/1994 | Locke et al. |
| 5,455,038 A | 10/1995 | Barney et al. |
| 5,583,262 A | 12/1996 | Maye et al. |
| 5,624,701 A | 4/1997 | Maye et al. |
| 5,827,895 A | 10/1998 | Nutter et al. |
| 6,083,254 A | 7/2000 | Evans et al. |
| 6,096,350 A | 8/2000 | Kemp et al. |
| 6,204,283 B1 | 3/2001 | Black et al. |
| 6,251,461 B1 | 6/2001 | Johnson et al. |
| 6,379,720 B1 | 4/2002 | Cooper et al. |
| 6,451,365 B1 | 9/2002 | King et al. |
| 6,475,537 B1 | 11/2002 | King et al. |
| 6,476,015 B1 | 11/2002 | Turos et al. |
| 6,620,446 B2 | 9/2003 | King et al. |
| 6,646,014 B2 | 11/2003 | Watkins |
| 6,702,645 B2 | 3/2004 | Vanderpool |
| 6,843,985 B2 | 1/2005 | Erickson, Jr. et al. |
| 7,087,849 B2 | 8/2006 | Brown et al. |
| 7,597,912 B2 | 10/2009 | Probasco |
| 7,879,348 B2 | 2/2011 | Volby |
| 8,153,146 B2 | 4/2012 | Probasco et al. |
| 2001/0014346 A1 | 8/2001 | Watkins |
| 2002/0051804 A1 | 5/2002 | Probasco et al. |
| 2002/0151249 A1 | 10/2002 | Scheuneman et al. |
| 2003/0060379 A1 | 3/2003 | Souter et al. |
| 2003/0129270 A1 | 7/2003 | Probasco et al. |
| 2003/0154508 A1 | 8/2003 | Stevens et al. |
| 2003/0215535 A1 | 11/2003 | Wilson et al. |
| 2004/0091558 A1 | 5/2004 | Lutz et al. |
| 2004/0131709 A1 | 7/2004 | Berdahl et al. |
| 2004/0175480 A1 | 9/2004 | Seman et al. |
| 2005/0031743 A1 | 2/2005 | Areso |
| 2005/0043404 A1 | 2/2005 | Probasco et al. |
| 2005/0049230 A1 | 3/2005 | Henrich et al. |
| 2005/0220914 A1 | 10/2005 | Probasco et al. |
| 2006/0009122 A1 | 1/2006 | Swanson |
| 2006/0009211 A1 | 1/2006 | Sato |
| 2006/0013870 A1 | 1/2006 | Kuhrts |
| 2007/0026765 A1 | 2/2007 | Renn |
| 2007/0232188 A1 | 10/2007 | Probasco |
| 2007/0264299 A1 | 11/2007 | Hughes et al. |
| 2008/0026673 A1 | 1/2008 | Probasco |

FOREIGN PATENT DOCUMENTS

| | | |
|---|---|---|
| EP | 0212623 A2 | 3/1987 |
| EP | 339147 A1 | 11/1989 |
| EP | 0441750 A1 | 8/1991 |
| EP | 0681029 A2 | 11/1995 |
| GB | 1058975 A | 2/1967 |
| GB | 2330076 | 4/1999 |
| JP | 57080304 A | 5/1982 |
| JP | 61031059 A | 2/1986 |
| JP | 05170625 A | 7/1993 |
| JP | 6098738 A | 4/1994 |
| WO | 94/09759 A2 | 5/1994 |

(Continued)

OTHER PUBLICATIONS

Jones, G., "Potential Control of Two-Spotted Spider Mite, *Tetranychus urticae* Koch, Using Hop b-Fraction," (1998) pp. 1-165, A thesis submitted for the degree of Doctor of Philosophy of the University of London and for the Diploma of Imperial College of Science, Technology & Medicine.

(Continued)

*Primary Examiner* — Michael Meller
(74) *Attorney, Agent, or Firm* — Edwards Wildman Palmer LLP; Jeffrey D. Hsi, Esq.; Melissa Hunter-Ensor, Esq.

(57) ABSTRACT

The invention provides compositions and methods for treating or preventing infestation of a site with a spider.

4 Claims, 1 Drawing Sheet

FOREIGN PATENT DOCUMENTS

| | | |
|---|---|---|
| WO | 97/33971 A1 | 9/1997 |
| WO | 99/09842 A1 | 3/1999 |
| WO | 01/06877 A1 | 2/2001 |

OTHER PUBLICATIONS

Losel, et al., The Potentional of Semidochemicals for Control of *Phorodon hummuli* (Homoptera: Aphididae), Pesticide Science, vol. 48, No. 4, pp. 293-303 (1996).

Jones et al., "Repellant and Oviposition-Deterring Effects of Hop-Beta Acids on the Two-Spotted Spider Mite *Tetranychus urticae*," Pesticide Science, vol. 47, No. 2, pp. 165-169 (1996).

"Culpeper's Complete Herbal A book of Natural Remedies for Ancient Ills,"Wordsworth Reference, pp. 134-135 (1995).

Simpson, W.J., "Synergism Between Hop Resins and Phosphoric Acid and its Relevance to the Acid Washing of Yeast", J. Inst. Brew., Sep.-Oct. 1987, vol. 93, pp. 405-406.

Simpson, W.J., "Studies on the Sensitivity of Lactic Acid Bacteria to Hop Bitter Acids", J. Inst. Brew., Sep.-Oct. 1993, vol. 99, pp. 405-411.

Simpson et al., "Factors Affecting Antibacterial Action of Hop Compounds and Their Derivatives", Journal of Applied Bacteriology, 72, pp. 327-334 (1992).

Newsletter of the Bayside Brewers Club, http://www.home.aone.net.au/bbc/bbcmay.html, pp. 1-7, May 1996.

Haas Products & Applications (http://www.john-i-haas.com/products/getinfo_products.htm?prod=isohop), 2001.

Kaneda et al., (Beer absorption on a Lipid Membrane as Related to Sen Evaluation), 2001, http://www.asbcnet.org/journal/pdfs/2001/0912-04R.pdf.

Hough et al., "Malting and Brewing Science: vol. II, Hopped Wort and Beer." Second edition. 1982, pp. 509-511.

Sammataro D., Parasitic mites of honey bees: life history, implications, and impact. Annu Rev Entomol. 2000;45:519-548.

International Search Report in PCT/US2007/23984, published Aug. 29, 2008.

International Search Report for Application No. PCT/US2009/000767 issued Mar. 30, 2009 and mailed Apr. 17, 2009.

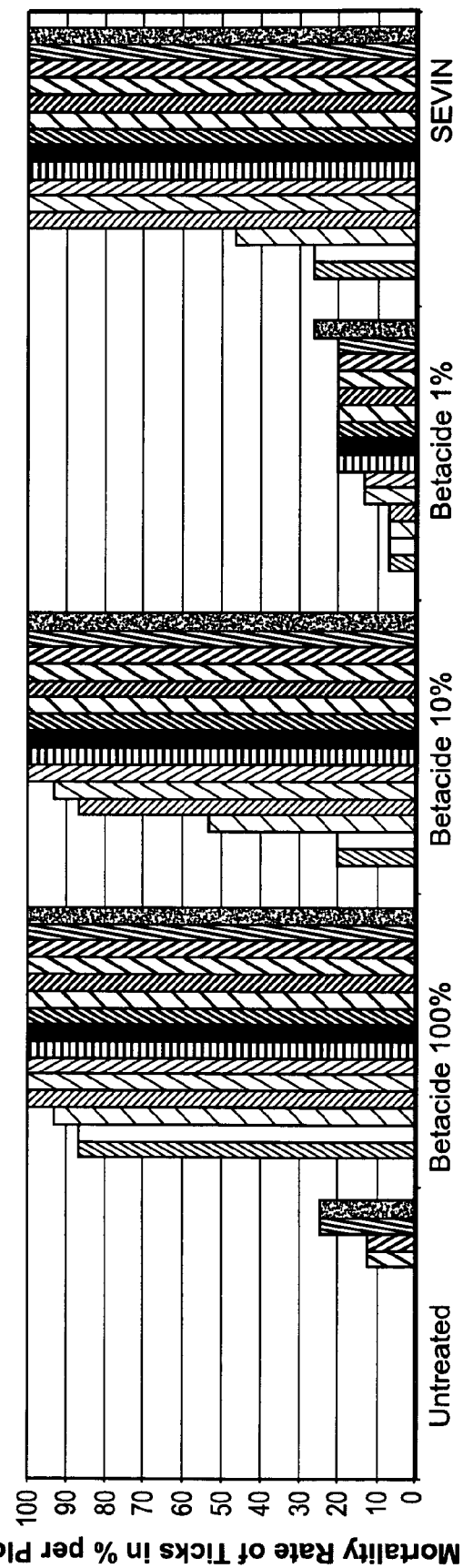
Graph 1. Mortality.
This graph illustrates the mortality rate of the American Dog Tick (*Dermacentor variabilis*) in percent per plot. Results for day 10 till day 15 remained the same.

COMPOSITIONS AND METHODS FOR ARACHNID CONTROL

CROSS-REFERENCE TO RELATED APPLICATION

This application is the U.S. national phase application, pursuant to 35 U.S.C. §371, of PCT international application Ser. No. PCT/US2009/000767, filed Feb. 6, 2009, designating the United States and published in English, which claims the benefit of U.S. Provisional Application No. 61/065,104, filed on Feb. 8, 2008 the entire contents of which are incorporated herein by reference.

BACKGROUND OF THE INVENTION

Arachnids are a class of arthropods that includes spiders, ticks, mites, and scorpions, which have segmented bodies that include two regions, but no antennae or wings. The anterior region of the arachnid includes four pairs of legs. Arachnida includes three principal orders: Araneina, or spiders; Arthrogastra, including scorpions, and Acarina, or mites and ticks. Ticks are blood-sucking acarid ectoparasites, which penetrate the skin of their host and feed on its blood. Ticks attack all groups of terrestrial vertebrates. Ticks are important vectors of a number of diseases, including Lyme disease, Rocky Mountain spotted fever, tularaemia, babesiosis, relapsing fever, erlichiosis, Colorado Tick Fever, typhus, hemorrhagic fever, and viral encephalitis. Conventional methods of tick control rely on reducing the population of animal hosts, such as the white tail deer that act as hosts for ticks that act as Lyme disease vectors, and spraying toxic chemicals in tick-infested areas. Despite these efforts, Lyme disease has been rising in many areas of the U.S., as the number of animal hosts has increased. Effective methods for controlling ticks, which do not involve the use of dangerous chemicals, are urgently required.

SUMMARY OF THE INVENTION

As described below, the present invention features compositions and methods for controlling arachnids.

In one aspect, the invention features a method of controlling a mammalian or avian parasitic arachnid, the method involving contacting the arachnid with an effective amount of a composition contains a hop derivative, thereby controlling the arachnid.

In another aspect, the invention features a method of controlling a tick or spider, the method involving contacting the tick or spider with an effective amount of a composition containing a hop derivative, thereby controlling the tick (e.g., *Amblyomma variegatum*, *Boophilus microplus*, *Boophilus annulatus*, *Dermacentor albipictus*, *Dermacentor variabillis*, *Dermacentor andersoni* Stiles, *Dermacentor variabilis*, *Ixodes cokkei* Packard, *Argas radiatus*, Raille, *Ornithodorus turicata*, *Ixodes scapularis*, Lone Star Tick, and *Rhipecephalus sanguineus*) or spider (e.g., black widow, brown recluse, or other spider). In one embodiment, the contacting occurs while the arachnid is in contact with a mammalian (e.g., humans, rodents, cattle, sheep, pigs, horses, dogs, and cats) or avian (turkeys, geese, ducks and chickens) host.

A method of treating or preventing a mammalian or avian parasitic arachnid infestation of a site (e.g., dwelling, field, feed lot, barn, or livestock pen), the method involving contacting the site with an effective amount of a composition containing a hop derivative, thereby treating or preventing the mammalian or avian parasitic arachnid infestation in the site. In one embodiment, the mammalian parasitic arachnid is a tick.

A method for preventing or reducing the transmission of a tick borne disease, the method involving contacting a host organism or site with a composition containing a hop derivative, thereby preventing or reducing the transmission of a tick borne disease (e.g., Rocky Mountain spotted fever, Tick paralysis, Tick-borne relapsing fever, Lyme disease, tularemia, babesiosis, and cattle tick fever). In one embodiment, the host is a mammal selected from the group consisting of humans, rodents, cattle, sheep, pigs, horses, dogs, and cats. In one embodiment, the host is an avian selected from the group consisting of turkeys, geese, ducks and chickens.

In another aspect, the invention features a composition for treating or preventing a mammalian or avian parasitic arachnid infestation, the composition containing an effective amount of a hop derivative in a suitable form for delivery to the arachnid.

In another aspect, the invention features for treating or preventing a tick or spider infestation, the composition containing an effective amount of a hop derivative in a suitable form for delivery to an arachnid.

In yet another aspect, the invention features a controlled release composition for treating or preventing a mammalian or avian parasitic arachnid infestation, the composition containing an effective amount of a hop derivative in a suitable form for delivery to a mammalian or avian parasitic arachnid infestation.

In another aspect, the invention features controlled release composition for treating or preventing a tick or spider infestation, the composition containing an effective amount of a hop derivative in a suitable form for delivery to a tick or spider.

In another aspect, the invention features a dusting powder containing hop acids, wherein the composition is suitable for delivery to a host organism or site of infestation for the treatment or prevention of a mammalian or avian parasitic arachnid infestation.

In another aspect, the invention features a shampoo containing an effective amount of hop acids, wherein the shampoo is suitable for treating or preventing a mammalian or avian parasitic arachnid infestation in a host organism.

In another aspect, the invention features a dip containing an effective amount of hop acids, wherein the dip is suitable for treating or preventing a mammalian or avian parasitic arachnid infestation in a mammalian host In another aspect, the invention features a host organism or site containing hop acids.

In another aspect, the invention features a product (e.g., meat, eggs, or milk) derived from a mammalian or avian host containing a hop derivative.

In another aspect, the invention features a kit for the treatment or prevention of mammalian or avian parasitic arachnid, the kit containing an effective amount of a hop acids in a form suitable for delivery to a host organism or site of infestation.

In another aspect, the invention features a kit for the treatment or prevention of a tick or spider infestation, the kit containing an effective amount of hop acids in a form suitable for delivery to a site of infestation. In one embodiment, the hop acids are formulated as a dusting powder, shampoo, or dip containing a hop derivative.

In another aspect, the invention features a method of identifying a hop derivative that disrupts a biological function of a pest selected from the group consisting of a mammalian or avian parasitic arachnid, tick and spider, the method involving contacting the pest with a test composition containing a hop derivative; and assaying a pest biological function. In one embodiment, the test compound disrupts a biological function in the pest or kills the pest.

In one embodiment, the method further involves contacting a host organism with the test composition; and assaying a host organism biological function. In another embodiment, the method identifies a test compound that does or does not disrupt a host organism biological function.

In another aspect, the invention features a method of controlling a spider (e.g., Salticidae, Pholcidae, Agelenidae, Araneus, Araneidae, Lycosidae Dysdera, Chemacanthium, Theridiidae, Latrodectus and Theraphosidael), the method involving contacting the spider with an effective amount of a composition containing a hop derivative, thereby controlling the spider. In one embodiment, the spider is infesting a structure, home, barn, yard, or other indoor or outdoor area.

In another aspect, the invention features a method of treating or preventing spider infestation of a site, the method involving contacting the site with an effective amount of a composition containing a hop derivative, thereby treating or preventing the spider infestation. In one embodiment, the site is a dwelling, field, feed lot, barn, or livestock pen.

In another aspect, the invention features a composition for controlling a spider infestation, the composition containing an effective amount of a hop derivative in an insecticidal excipient for delivery to the arachnid.

In another aspect, the invention features a controlled release composition for treating or preventing a spider infestation, the composition containing an effective amount of a hop derivative in a suitable form for delivery to a site of infestation. In one embodiment, the hop derivative is released over the course of at least 1, 3, 5, 7, or 14 days. In another embodiment, the hop derivative is released over the course of at least 30-60 days. In another embodiment, the composition has arachnicidal activity on contact.

In another aspect, the invention features dusting powder containing hop acids, wherein the dusting powder is suitable for delivery to a site of infestation.

In another aspect, the invention features a kit for control of spider infestation, the kit containing an effective amount of hop acids in a form suitable for delivery to a host organism or site of infestation.

In another aspect, the invention features a kit for the treatment or prevention of spider infestation, the kit containing an effective amount of hop acids in a form suitable for delivery to a site of infestation.

In another aspect, the invention features a method of identifying a hop derivative that disrupts a biological function of a spider, the method involving contacting the pest with a test composition containing a hop derivative; and assaying spider biological function (e.g., respiration, neural activity, locomotion, reproduction, or any other physiological activity required for arachnid survival).

In various embodiments of the above aspects, the composition contains at least 0.01% to 10% beta acids, at least about 0.03% beta acids or 3% Betacide, a combination of alpha and beta acids, at least about 0.1 to 10% alpha acids. In one embodiment, the contacting disrupts a biological function of an arachnid or kills the arachnid. In various embodiments, the hop acids or hop derivative is an alpha acid, beta acid, or combination of an alpha and a beta acid. In another embodiment, the hop derivative is formulated in a liquid, a powder, an oil, an emulsion, a capsule, a vapor, or a spray. In various embodiments of the above aspects, the composition further comprises a carrier. In various embodiments of the above aspects, the spider is a black widow, a brown recluse, or other dangerous spider.

Other features and advantages of the invention will be apparent from the detailed description, and from the claims.

DEFINITIONS

By "arachnid" is meant an eight legged arthropod.

By "alpha acid" is meant an organic acid derived from a hop plant (*Humulus lupulus*) having structural homology to a humulone, adhumulone, cohumulone, or an analog or derivative thereof. Humulone, adhumulone, and cohumulone are the three most abundant alpha acid analogs. Other exemplary derivatives of an alpha acid include, but are not limited to isoalpha acids, rhoisoalpha acids, tetrahydroisoalpha acids, and hexahydroisoalpha acids.

By "beta acid" is meant an organic acid derived from a hop plant (*Humulus lupulus*) having structural homology to a lupulone, adlupulone, colupulone or an analog or derivative thereof. Lupulone, adlupulone, and colupulone are the three most abundant beta acid analogs. Other exemplary derivatives of a beta acid include, but are not limited to, hulupones, hexahydrobeta acids and hexahydro hulupones.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "contacting" is meant touching, associating with, or having proximity to a composition.

By "controlling" is meant inhibiting the survival or reducing, slowing, or stabilizing the growth of a pest (e.g., mammalian or avian parasitic arachnid, tick, spider). Control is measured relative to an untreated pest or untreated population of pests.

By "effective amount" is meant an amount effective to disrupt a tick or other arachnid biological function.

By "hop derivative" is meant any molecule that naturally occurs in hops (*Humulus lupulus*) and chemical derivatives thereof. Hop derivatives (e.g., alpha acids, beta acids) may be purified from hops or may be chemically synthesized.

By "host" is meant an organism that is susceptible to infestation by a parasite.

By "infestation" is meant the colonization of a site or the parasitization of an organism by a pest.

By "mammalian or avian parasitic arachnid" is meant any arachnid capable of parasitizing a mammalian or avian host organism.

By "preventing an infestation" is meant reducing the probability that a pest infestation will be established in a host or in an area.

By "treating an infestation" is meant reducing, stabilizing, or slowing the growth of an existing infestation in a host or site.

By "site" is meant an environment that is susceptible to infestation by a pest. Exemplary sites include but are not limited to dwellings, live stock pens, barns, fields, woods, and yards.

BRIEF DESCRIPTION OF THE DRAWINGS

FIG. 1 is a graph showing the mortality rate of American Dog Tick (*Dermacentor variabilis*) in percent per plot. Results for day 10 till day 15 remained the same.

DETAILED DESCRIPTION OF THE INVENTION

The invention features compositions and methods that are useful for the treatment or prevention of an arachnid infestation in a host organism or area (e.g., building or outdoor area). The invention is based, at least in part, on the discovery that hop beta acids are as effective as conventional chemical insecticides in rapidly killing ticks and spiders.

Ticks

Ticks are blood-sucking parasites, which act as vectors for human and animal diseases. Frequently transmitted organisms include parasitic worms, viruses, bacteria, spirochetes, which cause Lyme disease, and rickettsias, which cause Rocky Mountain spotted fever. Ticks rapidly reproduce and can infest human dwellings, agricultural buildings, wooded areas and open fields. There are a number of tick species affecting various host organisms. The Brown Dog Tick's (*Rhipecephalus sanguineus*) most common host is the domestic dog. Adult ticks latch onto a host, feed on its blood, and when fully engorged, drop from the host to lay their eggs. Tick eggs, larvae, nymphs, and adults can rapidly infest human dwellings, where they hide behind baseboards, under window and door moldings, in carpets and floor coverings, and in furniture. The dog tick can lay 5,000 eggs within three days after dropping from a host. Eggs usually hatch in about three weeks depending on environmental conditions. The American Dog Tick *Dermacentor variabillis* is also found on dog hosts, but these ticks can survive on a variety of other large animal hosts. The American dog tick is a vector for Rocky Mountain spotted fever and is commonly associated with tick paralysis. Tick paralysis typically effects children. The cause of the paralysis is thought to be a toxin released into the blood stream by the tick during the feeding process. The toxin enters the bloodstream and causes an ascending paralysis, which starts in the lower body and moves into the upper body. The Rocky Mountain Wood Tick *Dermacentor andersoni* Stiles is found throughout the Rocky Mountain region and is the principal vector for Rocky Mountain spotted fever. Rocky Mountain spotted fever is caused by *Rickettsia rickettsii* (*R. Rickettsii*), which is carried by the ticks. The Groundhog Tick *Ixodes cokkei* Packard is most common in the New England states where they are found in summer cottages around areas frequented by groundhogs. The Common Fowl Tick *Argas radiatus* Raillet is a soft tick common in poultry houses. It may injure or even kill chickens, and may attack humans. *Ornithodorus turicata* is a group of soft ticks, which transmit bacteria *Borrelia recurrentis* and *Borrelia duttoni*, which cause relapsing fever. Relapsing fever is an infection caused by two similar bacteria in the Borrelia family. Tick-borne relapsing fever (TBRF) is transmitted by the *Ornithodoros tick*. Louse-borne relapsing fever (LBRF) is transmitted by body lice. The Blacklegged tick *Ixodes scapularis* (previously known as the Deer Tick *Ixodes dammini*) is a carrier of Lyme disease. The Lone Star Tick is a known vector for tularemia, Rocky Mountain spotted fever, and tick paralysis in dogs and humans. Other diseases transmitted by ticks include babesiosis, which is caused by the protozoan *Babesia microti*, and erlichiosis caused by a *rickettsia* belonging to the genus *Erlichia*. Ticks that typically select livestock hosts, such as cattle, horses, and other live stock, include the cattle tick (*Boophilus microplus* and *Boophilus annulatus*), which transmit cattle tick fever, *Dermacentor albipictus*, and the tropical bont tick (*Amblyomma variegatum*).

Spiders

Although spiders are primarily beneficial, they can become pests when they enter the home or other structures. For example, Jumping spiders (Salticidae), Cellar spiders (Pholcidae) can be a nuisance when they infest the home. A number of spiders that commonly infest homes produce painful bites. Funnel weaver spiders (Agelenidae) produce dense mats of silk in areas such as shrubs, thick grass, or corners of buildings. Funnel-web spider bites are extremely painful. Funnel weaver spiders usually cause tingling or numbness in the mouth or lips within 10-15 minutes. These bites can be very dangerous and may require medical treatment. Another spider that produces a painful bite is *Dysdera crocata* (Wood Louse Hunter), Araneus spiders (Araneidae), Wolf spiders (Lycosidae) are generally harmless, but the large species can bite.

Sac spiders spend daylight hours in a flattened silken sac, typically located in the upper corners of rooms or in wall cracks. They are usually the most common spider found wandering in homes during fall, particularly at night. *Chemacanthium* species are suspected as being the most common source of spider bites in homes. Cobweb spiders/House spiders (Theridiidae) are common inhabitants of dark corners around the home. They have a generally bulbous body and create messy webs with sticky threads. The majority of these spiders are harmless, although some are dangerous.

Dangerous Spiders

Widow Spiders (*Latrodectus*), such as the Back Widow Spider can inflict a painful bite which can be fatal, especially to the young and elderly. Only a small amount of venom from this spider can cause serious illness because the poison attacks the nervous system. Systemic envenomisation usually results in headache, nausea, vomiting, abdominal pain, pyrexia and hypertension. The Brown Recluse is another dangerous spider. The brown recluse lives within loose, messy webs in dark corners of buildings. The venom of the brown recluse is damaging to human cells. Brown recluse bites can cause significant cutaneous injury with tissue loss and necrosis causing slow-healing, ulcerous wounds.

Hobo Spiders (or grass spiders) are another group of dangerous biting spiders. Although the bite of the hobo spider is initially painless, the bite quickly develops into a blister that breaks open to form an oozing ulceration. The most common reported symptom associated with hobo spider bites is severe headache. Other symptoms include nausea, weakness, fatigue, temporary memory loss and vision impairment. The bite of Mouse Spiders causes severe illness. The male mouse spider has large hard fangs which can cause a deep painful bite. Black House Spiders bites are poisonous but not lethal. Certain people bitten experience severe pain around the bite site, heavy sweating, muscular pains, vomiting, headaches and giddiness. Tarantulas (Theraphosidae) may produce a pinching bite if handled, but such bites are typically not dangerous. However, when agitated, tarantulas rake their abdomen with their hind legs to throw very fine abdominal hairs in the direction of danger. These hollow, needlelike, barbed hairs readily penetrate human skin to introduce a toxic material that can cause a serious skin rash, an allergic response, and possible anaphylactic shock.

Hop Derivatives

Arachnicidal ccompositions of the invention include one or more compounds derived from hops. A hop derivative is a compound that occurs naturally in a hop plant (*Humulus lupulus*) or is chemically derived (either through natural biosynthetic procesess (e.g., living organism metabolism (e.g., mammal, plant, bacteria)) or by synthetic processes using human intervention (e.g., chemical synthesis). Of particular interest are the hop acids. Hops contain two major organic acid classes, alpha acids and beta acids. Hop acids are the bitter acid components of hops that are used in beer making. There are three major analogs for alpha acids, humulone, cohumulone, and adhumulone, and three major analogs for beta acids, lupulone, colupulone, and adlupulone. The percentages of the analogs present in the alpha acids and beta acids are variety-dependent. Thus, hop derivatives and hop products typically contain one or a mixture of these analogs. The percentage of analog present is dependent on the hop variety used to produce the derivative or product. Alpha acids and beta acids can be prepared by purification from natural hops and also by chemical synthesis according to traditional methods. Exemplary hop derivatives include beta acids, hexahydrobeta acids, rhoisoalpha acids, isoalpha acids, tetrahydroisoalpha acids, hexahydroisoalpha acids, magnesium salts of rhoisoalpha acids, and magnesium salts of beta acids. Compositions comprising hop derivatives are also available commercially. John I. Haas, Inc. products containing hop derivatives include Betacide, Redihop®, Isohop®, tetrahydroisoalpha acids (Tetrahop Gold®), Hexahop Gold®, MgRIAA and MgBeta. The active ingredients in these products are beta acids, rhoisoalpha acids (RIAA), isoalpha acids (IAA), tetrahydroisoalpha acids (THIAA), hexahydroisoalpha acids (HHIAA), magnesium salts of rhoisoalpha acids (MgRIAA) and magnesium salts of beta acids (MgBeta), respectively. These products and/or hop derivatives are typically diluted to a desired concentration for use in the methods of the invention.

Plant extracts are often used for the purification of compounds from plants (e.g., hops). An extract can be prepared by drying and subsequently cutting or grinding the dried material. The term "extract" refers to a concentrated preparation of the essential constituents of a plant, such as hops. Typically, an extract is prepared by drying and powderizing the plant. Optionally, the plant, the dried plant or the powderized plant may be boiled in solution. The extract may be used in liquid form, or it may be mixed with other liquid or solid herbal extracts. Alternatively, the extract may be obtained by further precipitating solid extracts from the liquid form. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, counter-current extraction, turbo-extraction, or by carbon-dioxide supercritical (temperature/pressure) extraction. The extract may then be further evaporated and thus concentrated to yield by means of air drying, spray drying, vacuum oven drying, fluid-bed drying or freeze-drying, the extract product.

Crude extracts are tested for arachnicidal activity as described herein. Further fractionation of a positive lead extract having arachnicidal activity is necessary to isolate chemical constituents responsible for the observed effect. Thus, the goal of the extraction, fractionation, and purification process is the careful characterization and identification of a chemical entity within the crude extract that inhibits the growth or proliferation of an arachnid, such as a tick. Methods of fractionation and purification of such heterogeneous extracts are known in the art. If desired, compounds shown to be useful as arachnicides are chemically modified according to methods known in the art.

Numerous methods are available for the chemical synthesis of candidate compounds. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995); and M. Verzele and D. De Keukeleire, Chemistry and Analysis of Hop and Beer Bitter Acids, Elsevier: Amsterdam (1991). Chemically synthesized alpha and beta acids can be separated from a reaction mixture and further purified by a method such as column chromatography, high pressure liquid chromatography, or recrystallization. As can be appreciated by the skilled artisan, further methods of synthesizing the compounds herein will be evident to those of ordinary skill in the art. Additionally, the various synthetic steps may be performed in an alternate sequence or order to give the desired compounds.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention. As used herein, the compounds of this invention, including the compounds of formulae described herein, are defined to include derivatives. Derivatives include compounds of the invention that are modified by appending appropriate functionalities to enhance desired properties.

Acceptable salts of the compounds of this invention include those derived from acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic acid, may be employed in the preparation of salts useful as intermediates in obtaining the compounds of the invention and their acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

In some embodiments, compositions of the invention include hop acids salts (e.g., sodium, potassium, lithium, calcium, magnesium) having increased stability. These hop acid salt (e.g., sodium, potassium, lithium, calcium, magnesium) compositions are advantageously stable relative to hop acids produced by conventional methods, which are susceptible to degradation due to heat, light, and acid catalysis. Compositions of the invention remain stable under conditions that induce the degradation of other conventional hop acids. In particular, after 6 months to 1 year of storage, the compositions of the invention are expected to retain at least about 50%, 60%, 75%, 80%, or preferably at least about 90%, 95% or even 100% of the hop acids present at the time of application. Hop acid salts (e.g., sodium, potassium, lithium, calcium, magnesium) are typically present in a diluent or carrier at levels ranging from about 0.01% to about 95%. The methods herein contemplate administration of an effective amount of compound or compound composition to achieve the desired or stated arachnidicidal effect. Preferably, the hop acids active ingredient is combined with carrier materials to form a composition suitable for application to a tick host or to an area infested with ticks or susceptible to tick infestation.

The compounds may be used either alone or in combination with other active or inactive substances and may be applied by spraying, pouring, dipping, in the form of concentrated liquids, solutions, suspensions, powders and the like, containing such concentration of the active compound as is more suited for a particular purpose at hand. They may be applied, for example, in the form of dilute solution, in a suitable solvent directly to an area of pest infestation or an area susceptible to infestation or bound to a solid support for application in powder form In some embodiments, arachnicidal compositions of the invention include water soluble hop acid alkali metal salts (e.g., sodium, potassium, lithium salts) and water insoluble hop acid alkaline earth metal salts (e.g., calcium, magnesium) having increased stability. These hop acid alkali metal salt (e.g., sodium, potassium, lithium salts) and water insoluble hop acid alkaline earth metal salt (e.g., calcium, magnesium) compositions are advantageously stable relative to hop acids produced by conventional methods, which are susceptible to degradation due to heat, light, and acid catalysis. Compositions of the invention remain stable under conditions that induce the degradation of other conventional hop acids. In particular, after 6 months to 1 year of storage, the compositions of the invention are expected to retain at least about 50%, 60%, 75%, 80%, or preferably at least about 90%, 95% or even 100% of the hop acids present at the time of application. Surprisingly, hop β acid crystals are also resistant to degradation and exhibit increased stability. Accordingly, hop β acid crystals are also useful in the compositions and methods of the invention.

Water soluble hop acid alkali metal salts (e.g., sodium, potassium, lithium salts) and water insoluble hop acid alkaline earth metal salts (e.g., calcium, magnesium) are typically present in a diluent or carrier at levels ranging from about 0.01% to about 95%. The methods herein contemplate administration of an effective amount of compound or compound composition to achieve the desired or stated arachnicidal effect. Preferably, the amount of active ingredient (e.g., hop acid alkali metal salts, hop acid alkaline earth metal salts or combinations thereof) are combined with carrier materials (e.g., maltodextrin, cluster dextrin, corn starch, corn syrup solids, glucose, cyclodextrin, arabic gum, calaginan, inuline, partially hydrogenated soybean oil, cellulose, hydroxymethyl cellulose, hydroxyethyl cellulose, hydroxypropyl cellulose, rosin, hypomellose) to form a powder suitable for delivery. For some applications, arachnicides of the invention are formulated as liquids using diluents (e.g., water, other aqueous solutions, water miscible solvents (ethanol, cremophor, dimethylsulfoxide (DMSO), dimethylformamide (DMF), isopropanol (ITA) or glycerol, and other solvents) to form a solution or slurry.

A typical arachnicidal preparation will contain from about 0.01% to about 95% hop acid, where the bottom of the range is any integer between 0.01 and 94 and the top of the range is any integer between 0.02 and 95, where the hop acids are provided in a carrier (e.g., maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, hypomellose) that is suitable for use in methods of producing a product having arachnicidal activity. Where non-aqueous arachnicidal compositions are desired, the arachnicidal of the invention are preferably formulated with rosin or partially hydrogenated soybean oil. Such compositions may be used for the slow release of the active arachnicidal composition, for example, in an aqueous slurry. In still other embodiments, arachnicidal compositions of the invention are dispersed in cellulose powder. In each of the aforementioned embodiments, the hop acid alkali metal (e.g., sodium, potassium, lithium), alkaline earth metal salts (e.g., calcium, magnesium), or other hop acid salts are dispersed or dissolved in water, ethanol, or another diluent together with any one or more of maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, and hypomellose. The composition is then spray dried to facilitate the formation of particles less than 1 mm in size. Preferably, the conditions used for spray drying are adjusted such that the particles are at least about 1 µm, 5 µm, 10 µm, 25 µm, 50 µm, 75 µm, 100 µm, 150 µm, 200 µm, 500 µm, 1 mm, 2 mm, or 5 mm in size. The ratio of hop acids to carrier ranges between about 1:2 and 1:100. Preferred ratios include 1:2, 1:3, 1:4, 1:5, 1:6, 1:7, 1:8, 1:9, 1:10, 1:20, 1:30, 1:50, 1:75, and 1:100. Alternatively, compositions of the invention include at least about 0.01%, 0.03%, 0.05%, 1%, 10%, 20%, 30%, 50%, 60%, 75%, 80%, 90%, or 95% hop acid or hop acid alkali metal (e.g., sodium, potassium, lithium) or hop acid alkaline earth metal salts (e.g., calcium, magnesium) in a diluent or carrier. Not all of the hop acids need be in the metal form. Anywhere between 5% and 100% of the hop acids present in the composition are in the metal form at any given time, and between 95% and 0% are present as free acids. In various embodiments, a composition of the invention contains hop acids where 90% are present in the metal form and 10% are present in the acid form; 50% are present in the metal form and 50% in the acid form; and 10% are present in the metal form and 90% in the acid form.

In preferred embodiments, the preparation includes between 0.01 and 95% (e.g., 0.01, 0.02, 0.03, 0.04, 0.05, 0.1, 0.2, 0.3, 0.4, 0.5, 1, 2, 3, 4, 5, 6, 7, 8, 9, 10, 25%, 75%, 80%, 90%, 95%) hop acids in a carrier or diluent. Alternatively, such preparations contain from about 20% to about 80% hop acids. Compositions containing alpha or beta acids are manufactured by ordinary methods. Hop acids suitable for addition to products can be formulated as ordinary tablets, capsules, solids, liquids, emulsions, slurries, fine granules or powders, which are suitable for administration to products during their preparation, following preparation but prior to storage, or at any time prior to their sale to a vendor or consumer. Lower or higher amounts than those recited above may be required. The compositions delineated herein include the compounds of the formulae delineated herein, as well as additional arachnicidal agents if present, in amounts effective for inhibiting arachnid growth or survival. Arachnicidal compositions of the invention may be used in virtually any application where the inhibition of an arachnid is desired. For example, compositions of the invention are used to prevent, reduce, inhibit, slow or stabilize the growth, proliferation, or survival of an arachnid.

Lower or higher effective amounts than those recited herein may be required to effectively kill arachnids without adversely affecting a host organism. Specific amounts and treatment regimens are determined empirically as described herein. Compositions of the invention are also useful for preventing the establishment of a tick, spider, or mammalian or avian parasitic arachnid infestation, for treating an established arachnid infestation, and for maintaining the health of a host previously treated for a parasitic arachnid infestation.

Formulations

Hop derivatives can be provided to a host organism or to a site infested with tick, spider, or mammalian or avian parasitic arachnids in a number of convenient formulations. Formulations of the invention are used to target arachnids on the body of hosts or in a site of infestation. Desirably, the composition of the invention is active in a site for at least about one, two, three, five, ten, thirty, sixty, one hundred eighty, or two hundred forty days. This provides for the presence of the arachnicide for the entirety of the arachnid life cycle, which typically is completed over the course of three to four weeks. Where activity is maintained for a shorter period (e.g., seven, fourteen, twenty-one, or thirty days), repeated administration of a composition of the invention may be desired or required. Compositions that are active for longer periods (e.g., two, three, six, nine, or twelve months) are also envisioned. Such compositions may be used for the long-term treatment of or prevention of an arachnid infestation.

Formulations of the invention can be sprayed directly in an area of infestation or they can be bound to a solid support or encapsulated in a time release material. The method of the present invention is carried out by introducing into an arachnid (e.g., tick) a sufficient amount of an arachnicide to impair growth and/or viability of the target arachnid or tick and thereby decrease the population of that pest in an area or on a host. A formulation containing a hop acid is introduced to an area of infestation. In one embodiment, the formulation is sprayed on as a wet or dry formulation on the surface of material infected with a target arachnid (e.g., tick), or material susceptible to infestation with such a target pest. Alternately, the formulation can be applied wet or dry to an area of infestation where it can contact an arachnid (e.g., tick). In some instances, time-release formulations may find use, particularly for applications to animals, or areas, which are subject to reinfestation, such as animal quarters.

The method of introducing of the subject pesticide into the target pest can be by any method that reduces survival, reproduction, or growth of the arachnid (e.g., tick). In one embodiment, the pesticide is absorbed by the pest or is ingested. The formulations can be used as powders, soaps or detergents for treatment of infestations of animals or humans, including infestations with ticks. In some instances it may be necessary to adjust the treatment formulation so as to reduce any dermatological effects associated with the treatment. Infestations of target pests can be treated using powder or detergent formulations, for example as a carpet shampoo to treat infestations of ticks. If desired, the hop acids are provided in a bait or trap, which can additionally can include a chemoattractant for the target pest (e.g., tick).

Further, this invention provides various methods of topically administering such compositions to the skin, hair or feathers of animals, in particular to mammals and birds, for reducing an established infestation and for inhibiting the transmission of ticks from one host to another, and to prevent the spread of diseases carried by such pests. The present invention, therefore, provides wash or topical skin solutions that are useful as "dips" in which the animal can be immersed, or as pour-on or spot-on formulations containing hop acids, which are intended to be applied topically to mammals, such as cattle, sheep, pigs, horses, dogs, cats, and the like, and to birds including poultry, such as turkeys, geese, ducks and chickens. In another approach, a hop derivative is provided in an encapsulated formulation (liquid or powder). Preferably, a hop derivative in liquid or powder form is encapsulated in a coating that breaks down slowly on a host or in an area infested with ticks or other arachnids. The coating provides for the long-term release of the hop derivative. Preferably, the composition is released over the course of two to six weeks (e.g., two, three, four, five, six weeks).

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of arachnicides. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the hop derivative is provided in an oil-based delivery system. The oil-hop derivative mix is deposited on a solid substrate and the substrate containing the hop derivative is placed into an area or on a host where it subsequently contacts and kills the ticks. Oil release substrates include vegetable and/or mineral oils. In one embodiment, the substrate also contains a surface active agent that renders the composition readily dispersable in water; such agents include wetting agents, emulsifying agents, dispersing agents, and the like.

Arachnicides of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion.

In other embodiments, arachnicides are prepared in a dusting composition or as a powder. Dusting compositions are typically prepared by grinding a composition comprising hops to a fine powder or by spray drying. The skilled artisan adjusts the conditions used in the spray drying process to achieve particles or granules of a size that facilitates delivery to a host or to a tick or other arachnid. Desirably, the powder comprises fine particles that coat the host or tick and all of its body parts. The dusting composition can be applied directly to a host or to a site where tick control is desired.

Alternatively, the arachnicides are prepared in a liquid spray composition that is formed by dispersing hops acids in any suitable liquid. Preferably, the hops acids are dispersed in water. If desired, the spray composition also includes a surfactant that allows the spray to be dispersed efficiently without clogging the spraying apparatus. The composition can be used to spray a host organism or an area where tick control is desired.

For livestock, the process consists of applying the solution to the animals in pastures and/or before they arrive in pasture or consists of in applying the solution to the animals before they arrive in the "feed lot". Because hop acids are Generally Regarded As Safe (GRAS), formulations of the invention may advantageously be used on live stock up to the time of slaughter and may be to treat animals used in milk or egg production without concern that such food products will be contaminated by toxic chemicals.

The compounds may be used either alone or in combination with other active or inactive substances and may be applied by spraying, pouring, dipping, in the form of concentrated liquids, solutions, suspensions, powders and the like, containing such concentration of the active compound as is more suited for a particular purpose at hand. They may be applied, for example, in the form of dilute solution, in a suitable solvent directly to an area of pest infestation or an area susceptible to infestation or bound to a solid support for application in powder form or in a "trap".

For use as a means of cleansing a surface, such as a carpet, pet bedding, pet fur and the like, although the hops can be formulated alone as an aqueous solution, it also can be prepared as a soap or a detergent. Detergents which can be used include anionic detergents, such as those described in U.S. patent application Ser. No. 4,978,686. The resulting emulsion is diluted to an appropriate concentration for use, and is additionally provided as a formulation suitable for the intended application, i.e. carpet shampoo, detergent, or animal shampoo or soap including shampoo or soap for human use.

For applications the formulation may be provided in a trap or as bait for a particular pest, the formulations of the subject invention can be sprayed directly in an area of infestation or they can be bound to a solid support or encapsulated in a time release material.

The method of the present invention is carried out by introducing into a target pest a sufficient amount of a pesticide to impair growth and/or viability of the target pest and thereby decrease the population of that pest in an area. A formulation containing the pesticide is introduced to an area of infestation. For example, the formulation is sprayed on as a wet or dry formulation on the surface of organic material infected with a target pest, or organic material susceptible to infestation with a target pest. Alternately, the formulation can be applied wet or dry to the an area of infestation where it can contact the target pest. In some instances, time-release formulations may find use, particularly for applications to animals, or areas which are subject to reinfestation, such as animal quarters.

In another approach, arachnicides of the invention are delivered in the form of a vapor.

Kits

The invention provides kits for the treatment or prevention of tick or other arachnid infestation. In one embodiment, the kit includes a composition containing an effective amount of a hop derivative in a form suitable for delivery to a site of infestation (e.g., host organism, building, or area). In some embodiments, the kit comprises a container, which contains an arachnicide; such containers can be boxes, ampoules, bottles, vials, tubes, bags, pouches, blister-packs, or other suitable container forms known in the art. Such containers can be made of plastic, glass, laminated paper, metal foil, or other materials suitable for holding arachnicides.

If desired the arachnicide of the invention is provided together with instructions for administering it to a site of infestation. The instructions will generally include information about the use of the composition for the treatment or prevention of an arachnid infestation. In other embodiments, the instructions include at least one of the following: description of the arachnicide; dosage schedule and administration for treatment or prevention of an arachnicide infestation; precautions; warnings; description of research studies; and/or references. The instructions may be printed directly on the container (when present), or as a label applied to the container, or as a separate sheet, pamphlet, card, or folder supplied in or with the container.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The following examples are provided to illustrate the invention, not to limit it. Those skilled in the art will understand that the specific constructions provided below may be changed in numerous ways, consistent with the above described invention while retaining the critical properties of the compounds or combinations thereof.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Hop Beta Acids Kill Ticks

The study consisted of five treatments: BetaCide, a composition comprising as an active ingredient 10% beta acids, was applied to the interior of three Petri dishes at 1, 10, and 100% volume per volume (v/v); Sevin was applied at 3 fl oz per gal (2.34% v/v), and an untreated check (UTC) with each treatment replicated three times. For each treatment, the interior of three Petri dishes was sprayed 4-5 times, with five ticks being placed into each dish, with a total of 15 ticks total per treatment. Evaluations determined numbers of ticks that were dead or alive over 7 intervals for the first 32 hours and then daily for days 2-15. Mortality rates were calculated in percent from these counts.

At 12 hours after exposure to the treatments, tick mortality was determined. The following percent mortalities were observed: UTC—0, BetaCide at 1%-6.7%, BetaCide at 10%-87%, BetaCide at 100%-100%; and Sevin—100%. With the exception of BetaCide 1%, treatments were significantly different from the UTC. For BetaCide 10%, mortality at 24 hours was 93% and at 32 hours was 100%. Mortality in BetaCide 1%, increased from 6.7% to 20% by day 2 and remained at that level through day 9 until day 10 when it increased to 27%. It stayed at that level through day 15, at which point the study was completed. The first mortality in the UTC occurred at day 7 at 12.5% and increased to 37.5% by day 15.

BetaCide, at 10 and 100%, had good efficacy against the American Dog Tick (*Dermacentor variabilis*). Betacide 100% was comparable with Sevin (carbaryl) at 2.3% (3 fl oz/gal).

Evaluations consisted of determining the amount of ticks that were dead and alive over different timed intervals and calculating the mortality rate in percent. Results of these studies are shown in Tables 1-3.

TABLE 1

Mortality. Mortality rate of American Dog Tick (*Dermacentor variabilis*) in percent (0-32 Hours).

| Treatment | Rate | Mortality Rate of Ticks in % | | | | | | |
|---|---|---|---|---|---|---|---|---|
| | | 0 hours | 2 hours | 4 hours | 8 hours | 12 hours | 24 hours | 32 hours |
| 1 Untreated | | 0 a | 0 b | 0 b | 0 c | 0 b | 0 c | 0 c |
| 2 Betacide | 100% V/V | 0 a | 86.67 a | 86.67 a | 93.3 a | 100 a | 100 a | 100 a |
| 3 Betacide | 10% V/V | 0 a | 20 b | 20 b | 53.3 b | 86.67 a | 93.33 a | 100 a |
| 4 Betacide | 1% V/V | 0 a | 6.67 b | 6.67 b | 6.67 c | 6.67 b | 13.33 b | 13.33 b |
| 5 SEVIN | 3 FL OZ/GAL | 0 a | 26.67 b | 26.67 b | 46.7 b | 100 a | 100 a | 100 a |

Means followed by same letter do not significantly differ (P = .05, Student-Newman-Keuls)
Mean comparisons performed only when AOV Treatment P(F) is significant at mean comparison OSL.

TABLE 2

Mortality. Mortality rate of American Dog Tick (*Dermacentor variabilis*) in percent (Day 2-Day 8).

| Treatment | Rate | Mortality Rate of Ticks in % | | | | | | |
|---|---|---|---|---|---|---|---|---|
| | | Day 2 | Day 3 | Day 4 | Day 5 | Day 6 | Day 7 | Day 8 |
| 1 Untreated | | 0 c | 0 c | 0 c | 0 c | 0 c | 12.5 b | 12.5 b |
| 2 Betacide | 100% V/V | 100 a | 100 a | 100 a | 100 a | 100 a | 100 a | 100 a |
| 3 Betacide | 10% V/V | 100 a | 100 a | 100 a | 100 a | 100 a | 100 a | 100 a |
| 4 Betacide | 1% V/V | 20 b | 20 b | 20 b | 20 b | 20 b | 20 b | 20 b |
| 5 SEVIN | 3 FL OZ/GAL | 100 a | 100 a | 100 a | 100 a | 100 a | 100 a | 100 a |

Means followed by same letter do not significantly differ (P = .05, Student-Newman-Keuls)
Mean comparisons performed only when AOV Treatment P(F) is significant at mean comparison OSL.

TABLE 3

Mortality. Mortality rate of American Dog Tick (*Dermacentor variabilis*) in percent (Day 9-Day 15).

| Treatment | Rate | Mortality Rate of Ticks in % | | | | | | |
|---|---|---|---|---|---|---|---|---|
| | | Day 9 | Day 10 | Day 11 | Day 12 | Day 13 | Day 14 | Day 15 |
| 1 Untreated | | 25 b | 25 b | 25 b | 25 b | 25 b | 25 b | 37.5 b |
| 2 Betacide | 100% V/V | 100 a | 100 a | 100 a | 100 a | 100 a | 100 a | 100 a |
| 3 Betacide | 10% V/V | 100 a | 100 a | 100 a | 100 a | 100 a | 100 a | 100 a |
| 4 Betacide | 1% V/V | 20 b | 26.67 b | 26.67 b | 26.7 b | 26.67 b | 26.67 b | 26.67 b |
| 5 SEVIN | 3 FL OZ/GAL | 100 a | 100 a | 100 a | 100 a | 100 a | 100 a | 100 a |

Means followed by same letter do not significantly differ (P = .05, Student-Newman-Keuls)
Mean comparisons performed only when AOV Treatment P(F) is significant at mean comparison OSL.

Example 2

Hop Beta Acids Kill Ticks in a Site of Infestation

This study consisted of one foliar application of a solution of Betacide (10% beta acids), which were diluted as described below and applied as a foliar spray to a 4 meter by 6 meter plot. Each plot was treated with one of the following treatments:

BetaCide at a rate of 100% v/v
BetaCide at a rate of 10% v/v
BetaCide at a rate of 1% v/v
Sevin at a rate of 3 fl oz/gal
Untreated Check (UTC).

| Trt No. | Treatment Name | Form Conc | Form Unit | Rate | Rate Unit | Other Rate | Other Rate Unit | Appl Code |
|---|---|---|---|---|---|---|---|---|
| 1 | Untreated | | | | | | | |
| 2 | Betacide | 10 | % | 100 | % V/V | 1860 | FL OZ/A | A |
| 3 | Betacide | 10 | % | 10 | % V/V | 186 | FL OZ/A | A |

-continued

| Trt No. | Treatment Name | Form Conc | Form Unit | Rate | Rate Unit | Other Rate | Other Rate Unit | Appl Code |
|---|---|---|---|---|---|---|---|---|
| 4 | Betacide | 10 | % | 1 | % V/V | 18.6 | FL OZ/A | A |
| 5 | SEVIN | 25 | % | 3 | FL OZ/GAL | 3 | FL OZ/GAL | A |

Replications: 3,
Design: Randomized Complete Block,
Treatment units: US standard,
Treated plot size Width: 4 meters,
Treated plot size Length: 6 meters,
Application volume: 14.5 gal/ac,
Mix size: 1 liters,
Format definitions: G-AII7.DEF, G-AII7.FRM The effects of this treatment on tick mortality were monitored. The results of this experiment on tick mortality per plot are shown in FIG. 1.

Example 3

Hop Beta Acids Kill Spiders

A 3% volume/volume aqueous solution of Betacide (10% hop acids) was applied to spiders in each of 10 petri dishes as a spray using C02 as a propellant. The 3% Betacide treatment showed high contact activity. A 3% aqueous solution of Betacide (10% hop acids) killed all spiders within one hour of contact.

Example 4

Hop Beta Acids Kill Funnel Spiders

A solution of Betacide (10% hop acids) was applied to funnel spiders infesting shrubs. The solution killed the spiders on contact.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of killing or repelling a tick on a host or a spider which is infesting a home, barn, yard, outdoor area or indoor area wherein the spider is selected from the group consisting of black widow, brown recluse, black house spiders, tarantulas, mouse spiders, hobo spiders, cobweb spiders, house spiders, sac spiders, wolf spiders, wood louse hunter, jumping spiders, cellar spiders, and funnel weaver spiders, the method comprising contacting said tick on a host or spider which is infesting a home, barn, yard, outdoor area or indoor area with an effective amount of a purified hop compound to kill or repel the spider or tick wherein the purified hop compound is selected from the group consisting of humulone, cohumulone, adhumulone, rhoisoalpha acids, isoalpha acids, tetrahydroisoalpha acids, hexahydroisoalpha acids, lupulone, colupulone, adlupulone, and hexahydrobeta acids, thereby killing or repelling the tick or spider, wherein said tick or spider is not a mite.

2. The method of claim 1, wherein the host is a mammalian or avian host.

3. The method of claim 2, wherein the mammalian host is a human, rodent, cattle, sheep, pig, horse, dog, or cat.

4. The method of claim 2, wherein the avian host is a turkey, goose, duck or chicken.

* * * * *